United States Patent [19]

Eikenberry

[11] Patent Number: 4,547,465

[45] Date of Patent: * Oct. 15, 1985

[54] ANALYTICAL ELEMENT HAVING IMPROVED SPREADING ZONE AND METHOD OF USE

[75] Inventor: Jon N. Eikenberry, Rochester, N.Y.

[73] Assignee: Eastman Kodak Company, Rochester, N.Y.

[*] Notice: The portion of the term of this patent subsequent to Oct. 15, 2002 has been disclaimed.

[21] Appl. No.: 600,646

[22] Filed: Apr. 16, 1984

[51] Int. Cl.$^4$ .......................... C12Q 1/32; C12Q 1/48; G01N 33/52

[52] U.S. Cl. ............................ 436/170; 422/56; 422/57; 435/15; 435/26; 435/805

[58] Field of Search .................................. 422/55–58; 436/169, 170, 175; 435/15, 16, 26, 805

[56] References Cited

U.S. PATENT DOCUMENTS 3,014,810  12/1961  Dybalski et al. .
3,992,158  11/1976  Przybylowicz et al. .
4,050,898  9/1977   Goffe et al. .
4,069,017  1/1978   Wu et al. .
4,153,668  5/1979   Hill et al. .
4,292,272  9/1981   Kitajima et al. ............... 422/56 X
4,303,408  12/1981  Kim et al. ...................... 422/57 X

FOREIGN PATENT DOCUMENTS 2085581  4/1982  United Kingdom .

Primary Examiner—Arnold Turk
Attorney, Agent, or Firm—J. Lanny Tucker

[57] ABSTRACT

A dry element capable of use for the analysis or transport of liquids comprises an isotropically porous zone which comprises a blush polymer having dispersed therein a particulate material and a nonpolymeric heterocyclic, aliphatic or carbocyclic quaternary ammonium compound comprising at least 12 carbon atoms therein. This compound is present in the porous zone in an amount of at least about 2 weight percent, based on the dry weight of the blush polymer. The porous zone of this element has improved cohesive strength which improves its resistance to abrasion. The element can be used to determine an analyte in an aqueous liquid, such as biological fluids.

20 Claims, No Drawings excellent# ANALYTICAL ELEMENT HAVING IMPROVED SPREADING ZONE AND METHOD OF USE

RELATED APPLICATION

Reference is made to my copending and commonly assigned application U.S. Ser. No. 600,641, filed on even date herewith and entitled MULTIZONE ANALYTICAL ELEMENT AND METHOD FOR ANALYTE DETERMINATION

FIELD OF THE INVENTION

This invention relates to a dry element useful for the chemical analysis or transport of water, foodstuffs and biological liquids. In particular, it relates to dry analytical elements which have improved manufacturability. This invention also relates to a method of using such elements for determination of an analyte.

BACKGROUND OF THE INVENTION

Chemical analysis of water, foodstuffs like milk and biological fluids such as serum and urine is often desirable or necessary. Various analytical elements to facilitate such analyses are known. Generally, such elements include a reagent (hereinafter termed interactive composition), for a substance under analysis (hereinafter termed analyte). The interactive composition, upon contact with a liquid sample containing the analyte, effects a detectable change in response to the presence of the analyte. For example, such a detectable change can be the formation or disappearance (e.g. reduction) of a detectable species, e.g. a dye. Such a change can be determined as it occurs (i.e. a rate assay), or after a certain time (i.e. endpoint assay).

Recently, much work has been directed toward developing dry analytical elements useful in diagnostic chemical analysis of biological fluids which provide highly quantitative results quickly and conveniently. For example, U.S. Pat. No. 3,992,158 (issued Nov. 16, 1976 to Przybylowicz et al) describes integral analytical elements which are a significant advance in the clinical chemistry art. These elements generally contain an isotropically porous spreading zone, also known as a fluid metering zone, which uniformly distributes a liquid sample throughout the zone. A variety of useful spreading zones are described in that reference. In one embodiment, the spreading zone is composed of a "blush" polymer which has a particulate material dispersed therein. Such elements are manufactured using conventional coating and drying techniques, and subsequently slitting or chopping the dried layer. However, during such mechanical handling operations, it has been observed that the dry blush polymer layers are sensitive to abrasion, and objectionable flaking or dust is generated particularly during slitting and chopping operations. Not only is the dust an environmental hazard, but this abrasion sensitivity often leads to unacceptable product when the dried spreading layer has ragged edges or crumbles during slitting. Attempts have been made to improve spreading layer abrasion resistance by increasing the blush polymer coverage or by reducing the amount of non-solvent (defined hereinbelow) used during the coating operations. These efforts, however, have had limited success, and undesirably resulted in a loss of zone porosity or void volume and attendant long liquid spreading times.

U.S. Pat. No. 3,014,810 (issued Dec. 26, 1961 to Dybalski et al) relates to pigment compositions which can be incorporated in nonporous rubbers and plastics to provide nonporous finished products having improved hardness, tensile strength and other physical properties. The pigment compositions described therein include a mixture of two amine surface-active agents in a specified ratio. These surfactants allegedly reduce pigment agglomeration during storage and shipping and improve pigment dispersion in the hard rubbers and plastics. The first agent is a quaternary ammonium compound and the second is a tertiary amine. The mixture of surface-active agents described therein is not suitable for use in analytical elements containing various chemical reagents because the tertiary amine of the mixture is highly reactive with respect to reagents commonly employed in clinical chemistry analyses. There is no suggestion in this reference of any means for improving the cohesive strength of porous materials such as porous spreading layers used to transport liquids.

Hence, there is a need in the art for a porous spreading zone material which has improved cohesive strength and abrasion resistance but which retains desirable spreading properties and is inert to chemical reagents which may be incorporated therein.

SUMMARY OF THE INVENTION

The present invention provides an improved dry element which overcomes the abrasion problem observed in known elements. In particular, the elements of this invention comprise an isotropically porous zone comprising a blush polymer which has improved cohesive strength, and hence improved abrasion resistance. These elements are much more easily manufactured as they have less tendency to flake or chip during slitting and chopping operations. Because of the improved abrasion resistance, reduction of hazardous dust and defective product produced during manufacture are achieved. These improvements are achieved by incorporating one or more of a particular class of quaternary ammonium compounds within the porous zone of the element.

Therefore, in accordance with this invention, a dry element for the analysis or transport of an aqueous liquid comprises an isotropically porous zone which comprises a blush polymer having dispersed therein a particulate material and a nonpolymeric heterocyclic, aliphatic or carbocyclic quaternary ammonium compound comprising at least 12 carbon atoms therein. This compound is present in the zone in an amount of at least about 2 weight percent, based on the dry weight of the blush polymer.

In preferred embodiments, these elements are dry analytical elements for determination of an analyte, and also contain an interactive composition for the analyte.

This invention also provides a method for the determination of an analyte in an aqueous liquid using the dry analytical element of this invention. This method comprises the steps of:

A. physically contacting a sample of the liquid together with an interactive composition for the analyte and an element described hereinabove to provide a detectable change; and B. measuring the detectable change.

DETAILED DESCRIPTION OF THE INVENTION

The elements of this invention comprise an isotropically porous zone. This zone is often termed a spreading or metering zone in the art because of its ability to spread, meter or transport applied liquid samples rapidly therein. Isotropic porosity means that the zone is substantially porous to aqueous liquid in all directions within the zone. It will be understood that the degree of porosity can be variable within the zone. In the elements of this invention, it is useful to have a void volume of at least about 25 percent of the total zone volume, and void volumes of 50 to 95 percent may be desirable in certain instances. As can be appreciated, void volume within the zone can be controlled, for example, by the selection of constituent materials, or by varying the solvents or drying conditions during preparation as described in more detail hereinbelow.

The isotropically porous zone can be in any suitable location in the element. It can be a self-supporting matrix so that the zone alone, or in combination with other zones, is structurally strong enough to be self-supporting. Preferably, however, the zone is carried on a suitable substrate (or support hereinafter) and is the outermost layer on that support so that the liquid sample to be assayed comes into contact with this porous zone before any other part of the element. For example, an element can comprise one or more zones or layers which perform functions other than spreading but which element has the described porous layer as an outermost spreading layer to bring a sample of an aqueous liquid into contact with those other zones or layers. Alternatively, the element can have one or more other spreading or metering zones, and the particular blush polymer porous zone described herein can be between these zones or between the support and all of the other zones. In such embodiments, another spreading zone is the outermost zone in the element.

The isotropically porous zone essential to the present invention comprises a "blush" polymer. Such polymers are generally formed on a support by dissolving a polymer in a mixture of two liquids, one of which is a lower boiling, good solvent for the polymer and the other which is a higher boiling non-solvent or poor solvent for the polymer. Such a polymer solution is then coated on the support and dried under controlled conditions. The lower boiling solvent evaporates more readily and the coating becomes enriched in the liquid which is the poor solvent. As evaporation proceeds under proper conditions, the polymer forms an isotropically porous layer as that term is used herein. Many different polymers can be used, singly or in combination, for preparing a blush polymer porous zone, including polycarbonates, polyamides, polyurethanes and cellulose esters. Cellulose acetate and polyurethane are preferred polymers in the practice of this invention either singly or in a mixture. The blush polymer (including mixtures of polymers) is generally present in the porous zone of this invention at a coverage of from about 2 to about 40, and preferably from about 5 to about 20, g/m$^2$. Solvent mixtures for preparing blush polymers are well known in the art. Further details for preparing blush polymers are provided in the art, e.g. in U.S. Pat. No. 3,992,158 (noted hereinabove).

The blush polymer porous zone of the elements of this invention has dispersed therein one or more fine particulate materials. Various types of particulate matter, all desirably chemically inert to the analytes and the interactive compositions used in the assays and generally in the form of a fine powder, are useful. Pigments, such as titanium dioxide, barium sulfate, zinc oxide, lead oxide, etc. are useful with titanium dioxide and barium sulfate being preferred. Other desirable particulate materials include silicates such as diatomaceous earth, microcrystalline colloidal materials derived from natural or synthetic polymers, and resinous or glass beads. Details of other useful particulate materials and methods of incorporating such in the blush polymer porous zone are provided, for example, in U.S. Pat. No. 3,992,158 (noted hereinabove) the disclosure of which is incorporated herein by reference in its entirety. The coverage of the particulate material in the porous zone is generally from about 20 to about 250, and preferably from about 40 to 120, g/m$^2$.

In the elements of this invention, the weight ratio of particulate material to blush polymer is from about 2:1 to about 20:1, and preferably from about 6:1 to about 15:1.

The advantage of improved cohesive strength exhibited by the elements of this invention is obtained by the incorporation of one or more nonpolymeric heterocyclic, aliphatic or carbocyclic quaternary ammonium compounds, each compound comprising at least 12 carbon atoms therein in the porous spreading zone. Such a compound is present in the spreading zone in an amount of at least about 2, preferably from about 8 to about 30, and more preferably from about 10 to about 25, weight percent, based on the dry weight of the blush polymer in the zone. As used herein, the term "nonpolymeric" means that the compounds are not composed of repeating quaternary ammonium cationic moieties and generally have a molecular weight of less than about 4000, and preferably less than about 2000.

As used herein, the term "heterocyclic" quaternary ammonium compound refers to an organic cationic ammonium compound having at least one heterocyclic moiety. The cationic charge can be either in the heterocyclic moiety or in another portion of the molecule. The heterocyclic moiety can be aromatic or nonaromatic, and can contain such heteroatoms as nitrogen, oxygen, sulfur, and selenium atoms. Generally, the heterocyclic moiety has from 5 to 20 atoms in its backbone.

The term "aliphatic" quaternary ammonium compound refers to an organic cationic ammonium compound which contains four aliphatic, or open-chain, moieties attached to the quaternary ammonium atom. The aliphatic moieties contain from 1 to 30 carbon atoms and can have oxygen atoms interspaced along the chain, provided such compound comprises at least 12 carbon atoms. Preferably, at least one of the aliphatic moieties has at least 6 carbon atoms, and more preferably, at least one moiety comprises at least 12 carbon atoms.

The term "carbocyclic" quaternary ammonium compound refers to an organic cationic ammonium compound which contains at least one carbocyclic moiety attached to the quaternary ammonium atom. Such carbocyclic groups include cycloalkyls generally of 5 to 20 carbon atoms, cycloalkenyls generally of 5 to 20 carbon atoms, cycloalkynyls generally of 5 to 20 carbon atoms, and aryls generally of 6 to 14 carbon atoms, in the cyclic backbone.

In preferred embodiments of this invention, heterocyclic, aliphatic and carbocyclic quaternary ammonium compounds can be represented by the structures (Ia and b):

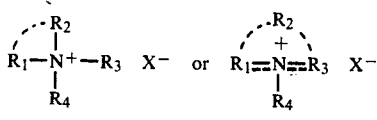

Ia.          Ib.

wherein ==== represents a single or double bond; $R_1$, $R_2$, $R_3$ and $R_4$ are independently substituted or unsubstituted alkyl, preferably of 1 to 30 carbon atoms (e.g. methyl, ethyl, chloroethyl, isopropyl, decyl, dodecyl, alkyl groups substituted with an alkylcarbonamido group, such as $C_{17}H_{35}CONH-$, alkyl groups substituted with a fluorocarbonsulfonamido group, such as $C_8F_{17}SO_2NH-$, etc.);

(alkylene-oxy$)_n$H wherein the alkylene comprises 2 to 6 carbon atoms and is substituted or unsubstituted, and n is an integer of 1 to 50 (e.g. ethyleneoxy, propoxy, etc.); substituted or unsubstituted aryl, preferably of 6 to 14 carbon atoms in the aromatic backbone (e.g. phenyl, xylyl, naphthyl, p-methoxyphenyl, etc.); substituted or unsubstituted cycloalkyl, preferably of 5 to 20 carbon atoms in the carbocyclic ring (e.g. cyclopentyl, cyclohexyl, etc.); substituted or unsubstituted alkaryl, preferably of 7 to 30 carbon atoms in the backbone (e.g. benzyl, 3-propylphenyl, etc.); or a fluorocarbon group, preferably having from 1 to 30 carbon atoms (e.g. perfluorohexyl, perfluorododecyl, etc.); provided that $R_1$, $R_2$, $R_3$ and $R_4$ together comprise at least 12 carbon atoms.

Alternatively, $R_1$ and $R_2$ taken together with the nitrogen atom, can form a quaternary heterocyclic ring, e.g. pyrrolidinium, piperidinium and the like, to form a heterocyclic amine having two pendant groups, $R_3$ and $R_4$, attached to the quaternary ammonium atom. This heterocyclic ring generally contains a total of 5 to 20 carbon atoms and heteroatoms (as defined hereinabove) in the ring backbone. The ring can be substituted with any of a number of moieties known to one skilled in the art. In this heterocyclic compound, $R_3$ and $R_4$ are as defined hereinabove but comprise at least 12 carbon atoms.

In another embodiment illustrated by structure Ib, $R_1$, $R_2$ and $R_3$, taken together with the nitrogen atom, can form a quaternary heterocyclic ring, e.g. pyridinium, quinolinium, pyrimidinium and the like to provide a heterocyclic amine having a single pendant group $R_4$. $R_4$ is as defined above also but comprises at least 12 carbon atoms. This heterocyclic amine generally contains 5 to 20 carbon atoms and heteroatoms (as defined hereinabove) in the ring backbone (e.g. pyridinium, quinolinium, acridinium, benzothiazolium, benzoxazolium, etc.). Preferably, $R_4$ is alkyl (as defined above) of 12 to 30 carbon atoms.

$X^-$ is any suitable monovalent anion, such as halide, nitrate, phosphate, sulfate and the like.

In a more preferred embodiment, $R_1$ is substituted or unsubstituted alkyl of 1 to 6 carbon atoms; $R_2$ is substituted or unsubstituted alkyl of 1 to 6 carbon atoms or (alkylene-oxy$)_n$H wherein alkylene has 2 to 4 carbon atoms and is substituted or unsubstituted; and $X^-$ is halide or nitrate.

The following list of useful quaternary ammonium compounds is not exhaustive of compounds useful in the practice of this invention, but it provides a representative sampling of useful compounds. Useful compounds include:

| Compound | Generic or tradename |
|---|---|
| $CH_3(CH_2)_8\overset{+}{N}(CH_3)_3$ $Br^-$ | Nonyltrimethyl ammonium bromide; |
| $CH_3(CH_2)_{11}\overset{+}{N}(CH_3)_3$ $Cl^-$ | Dodecyltrimethyl ammonium chloride; |
| $CH_3(CH_2)_{15}\overset{+}{N}(CH_3)_3$ $Br^-$ | Hexadecyltrimethyl ammonium bromide; |
| 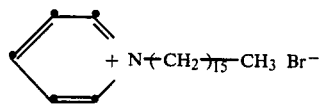 | Hexadecylpyridinium bromide; |
| 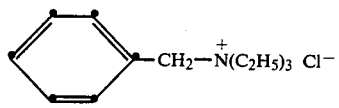 | Benzyltriethyl ammonium chloride; |
| $[CH_3(CH_2)_{11}]_2\overset{+}{N}(CH_3)_2$ $Br^-$ | Didodecyldimethyl ammonium bromide; |
| 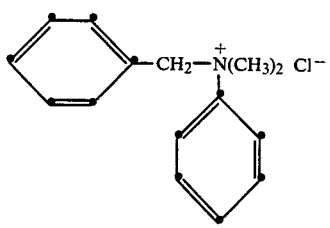 | Benzyldimethylphenyl ammonium chloride; |
| $[CH_3(CH_2)_5]_4\overset{+}{N}$ $Cl^-$ | Tetrahexyl ammonium |

-continued

| Compound | Generic or tradename |
|---|---|
| | chloride; |
| CH$_3$(CH$_2$)$_{17}$N$^+$(CH$_3$)$_2$ Cl$^-$<br>                                CH$_2$<br>                                 (phenyl) | Stearyldimethylbenzyl ammonium chloride; |
| H[OCH(CH$_3$)CH$_2$]$_n$OCH(CH$_3$)CH$_2$N$^+$(C$_2$H$_5$)$_2$ Cl$^-$<br>                                                    CH$_3$ | Polypropoxy quaternary ammonium chlorides | wherein n is 8, 25 or 41;

| | |
|---|---|
|          O            CH$_3$<br>         ‖            |$^+$<br>CH$_3$(CH$_2$)$_{16}$CNH(CH$_2$)$_3$NCH$_2$CH$_2$OH  NO$_3^-$<br>                                    CH$_3$ | Cyastat SN ™ (American Cyanamid, Wayne, New Jersey); |
| C$_{18}$F$_{37}$SO$_2$NHCH$_2$CH$_2$N$^+$(CH$_3$)$_3$ I$^-$ | Fluorad ™ (3M Company, St. Paul, Minnesota); |
| (R')$_2$N$^+$(CH$_3$)$_2$ Cl$^-$ | Dicocodimethyl ammonium chloride (Armak Industrial Chemicals, Chicago, Illinois) | which is a mixture of compounds wherein R' is alkyl of 12, 14 or 16 carbon atoms; and

| | |
|---|---|
| $\left[\begin{array}{c}(CH_2CH_2O)_xH\\ \|\\ R''-N^+-CH_3\\ \|\\ (CH_2CH_2O)_yH\end{array}\right]$ Cl$^-$ | Polyethoxylated quaternary ammonium chlorides. | wherein R" is alkyl of 8 to 18 carbon atoms, x and y are independently integers of 2 to 50.

The elements of this invention can include an interactive composition although the presence of such a composition is not required in the element for practice of this invention (e.g. it could be added in the liquid sample or as a separate sample). These compositions can be a single chemical compound or a combination of chemical compounds or reagents which can interact with the analyte, with a reaction decomposition product of the analyte, or with each other, upon contact with the analyte to produce a detectable change. Such interaction is meant to refer to chemical reactivity, catalytic activity as in the formation of an enzyme-substrate complex, antigen-antibody reaction and any other form of chemical or physical interaction that can produce or promote within the element, such as in a reagent or spreading zone, a change which is radiometrically detectable, that is by suitable measurement of light or any other energy form. For example, the change can be release of a preformed detectable species, the formation of a detectable species or the disappearance or reduction in amount of a detectable species. The change produced can be correlated to the amount of analyte in the liquid sample.

The particular interactive composition distributed within the element will depend on the analysis of choice. The composition useful for a given analysis would be within the skill of a worker in the clinical chemistry art. The elements of this invention can be adapted, for example, for the analysis of ground water, foodstuffs, and biological fluids, such as blood, plasma, serum, cerebral spinal fluid, urine and the like. Analyses of analytes, such as glucose, lactate, triglycerides, total protein, albumin, uric acid, bilirubin, creatine kinase, amylase, alkaline phosphatase, lactate dehydrogenase, alanine aminotransferase (ALT) and aspartate aminotransferase (AST) are but representative of the potential uses of the elements of this invention.

In one embodiment of this invention, the element is used to determine aspartate aminotransferase (AST) or alanine aminotransferase (ALT). The interactive composition for AST elements can include, for example, in quantities known by one skilled in the art, L-aspartate, α-ketoglutarate, NADH (nicotinamide adenine dinucleotide), lactate dehydrogenase, malate dehydrogenase and pyridoxal phosphate. Alternatively, other interactive compositions known for determining AST can be used.

An interactive composition useful in ALT elements includes, for example, in quantitites known by one skilled in the art, L-alanine, NADH, α-ketoglutarate, lactate dehydrogenase and pyridoxal phosphate. Alternatively, other interactive compositions known for determining ALT can be used, if desired.

The interactive composition can be placed in any suitable location in the elements of this invention. Where the element consists of a single porous spreading zone, the composition is in that zone in its entirety. However, where the element consists of multiple zones, the composition can be in any of the zones (e.g. a reagent zone), or the components of the composition can be distributed among two or more zones in the element.

The dry analytical elements of this invention have at least one porous spreading zone, i.e. the blush polymer zone described hereinabove. This zone can also be a spreading/reagent zone if it contains the interactive composition or some component thereof. This zone can be a self-supporting carrier matrix, but preferably it is carried on a separate support. Such a support is a film or sheet made of any suitable dimensionally stable, and preferably transparent (i.e. radiation transmissive) material which transmits electromagnetic radiation of a wavelength between about 200 and about 900 nm. Useful support materials include polystyrene, polyesters [e.g. poly(ethylene terephthalate)], polycarbonates, cellulose esters, etc.

The element can have a single zone or a plurality of zones (including spreading, reagent, subbing, buffer, reflective, barrier, etc. zones), some or all of which can contain reagents. These zones are in fluid contact with each other, meaning that fluids can pass between superposed regions of adjacent zones. Stated in another manner, fluid contact refers to the ability to transport components of a fluid between the zones in fluid contact. Preferably, the zones are separate coated layers, although one or more zones can be in a single layer, or one or more separate layers can be in a single zone, of an element. Dry element formats and materials are known in the art and described for example in U.S. Pat. No. 3,992,159 (noted hereinabove); U.S. Pat. No. 4,042,335 (issued Aug. 16, 1977 to Clément); U.S. Pat. No. 4,144,306 (issued Mar. 13, 1979 to Figueras); U.S. Pat. No. 4,132,528 (issued Jan. 2, 1979 to Eikenberry et al); U.S. Pat. No. 4,258,001 (issued Mar. 24, 1981 to Pierce et al); U.S. Pat. No. 4,292,272 (issued Sept. 29, 1981 to Kitajima et al); U.S. Pat. No. 4,430,436 (issued Feb. 7, 1984 to Koyama et al); Japanese Patent Publication No. 57(1982)-101760; and U.S. Pat. No. 4,450,232 (issued May 22, 1984 to Sanford et al).

Particularly useful elements for the determination of the transferases, AST and ALT, are illustrated in the examples hereinbelow.

The analytical method of this invention can be automated or manual. In general, an analyte in an aqueous liquid is determined by taking an element from a supply roll, slide packet or other source and physically contacting it with a sample of the liquid. Such contact can be accomplished in any suitable manner, e.g. dipping or immersing the element into the sample or, preferably, by spotting the element by hand or machine with a drop (e.g. about 1–20 μL) of the sample by pipette or another suitable dispensing means.

After sample application, the element is exposed to any conditioning, such as incubation, heating or the like, that may be desirable to quicken or otherwise facilitate obtaining any test result. The interactive composition will chemically react with any analyte present in the sample and produce a detectable change (as described hereinabove) which can be measured at an endpoint or as a rate change with suitable detection equipment and techniques. Such equipment includes conventional reflection, transmission or fluorescence spectrophotometers which are well known in the art.

The following examples illustrate the practice of this invention. In preparing the dry analytical elements, the components were obtained from the following sources: polyurethane resin (Estane TM 5715) from B. F. Goodrich (Cleveland, Ohio); Triton TM 405 surfactant from Rohm & Haas (Philadelphia, Pa.); Brij TM 98 surfactant from ICI Americas, Inc. (Wilmington, Del.); sodium α-ketoglutarate from Sigma Chemicals (St. Louis Mo.); sodium L-aspartate from ICN Nutritional Biochemicals (Cleveland, Ohio); lactate dehydrogenase, malate dehydrogenase and pyridoxal-5-phosphate from Boehringer Mannheim (Indianapolis, Ind.); NADH from P-L Biochemicals (Milwaukee, Wis.); polypropoxy quaternary ammonium chlorides as EMCOL TM CC36 and CC42 from Witco Chemical Corp. (New York, N.Y.); amylopectin starch from National Starch & Chemical Corp. (Buffalo, N.Y.); Drimarine Red Z2B dye from Sandoz Corp. (Hanover, N.J.), and the remainder from Eastman Organic Chemicals (Rochester, N.Y.) or from in-house sources.

The cohesive strength test used in the examples measures the distance, in millimeters, at which a sapphire stylus scribing the surface of the blush polymer spreading layer first produces a "flaking" of the layer so that the layer begins crumbling.

The test was carried out in the following manner: dried blush polymer spreading layers were conditioned at about 20° C. and 50% relative humidity for 1 hour. A 12×18 cm sample of the layer was then positioned under the stylus and the stylus was lowered to the surface of the spreading layer. The sample was mechanically moved under the lowered stylus for about 158 mm. The stylus arm was then raised and cleaned. This scribing procedure was repeated 5 times for each sample, each time at a different location on the sample. The distance of scribing at which "flaking" first occurred was then measured for each scribing, and the six measurements for each sample were averaged. "Flaking" refers to the breaking apart of the spreading layer and formation of flakes or pieces thereof.

EXAMPLES 1-3

Elements With Spreading Layers Having Improved Cohesion

Elements containing a blush polymer spreading layer were prepared on a poly(ethylene terephthalate) support. The spreading layer comprised the components noted in Table I hereinbelow. Control elements outside the scope of this invention were also prepared. In each case, the element prepared according to the present invention having a blush polymer spreading layer composed of a quaternary ammonium compound described herein exhibited significant improvement in cohesive strength over the Control element.

TABLE I

| Spreading Layer | Formulation | | Cohesive Strength (mm to flake) | % Improvement |
|---|---|---|---|---|
| Control A | Titanium dioxide | 20–200 g/m² | 43 | — |
| | Cellulose acetate | 3–30 g/m² | | |
| | Estane TM 5715 | 0.5–5 g/m² | | |
| | Brij TM 98 | 0.2–2 g/m² | | |
| | Triton TM X-405 | 0.4–4 g/m² | | |
| Example 1 | Same as Control A plus EMCOL TM -CC42 | 0.3–3 g/m² | 158+* | 267% |
| Control B | Barium sulfate | 25–250 g/m² | 19 | — |

TABLE I-continued

| Spreading Layer | Formulation | | Cohesive Strength (mm to flake) | % Improvement |
|---|---|---|---|---|
| | Cellulose acetate | 2.5–25 g/m² | | |
| | Estane ™ 5715 | 0.5–5 g/m² | | |
| | Triton ™ X-405 | 0.6–6 g/m² | | |
| Example 2** | Same as Control B plus EMCOL ™-CC36 | 0.3–3 g/m² | 103 | 442% |
| Example 3** | Same as Example 2 | | 41 | 116% |

*The cohesive strength testing device had a limit of 158. In this test, no flaking was seen for the entire length.
**In Example 2, EMCOL ™-CC36 was added to the spreading layer formulation by mix melting in the nonsolvent mixture used to blush the polymers. This procedure is preferred for quaternary ammonium compounds which are soluble in the nonsolvent mixture. In Example 3, EMCOL ™-CC36 was added as one of the components of the spreading layer dispersion during make up, rather than during the blushing procedure.

EXAMPLE 4

Element for Determination of Aspartate Aminotransferase (AST)

This is an example comparing an element useful for determining AST prepared according to this invention to a conventional element. The element of this invention had the format and components noted hereinbelow. The Control element was similarly made except N-hexadecylpyridinium bromide was omitted from the spreading/reagent layer.

| | | |
|---|---|---|
| Spreading/ Reagent Layer | Barium sulfate | 25–250 g/m² |
| | Cellulose acetate | 2.5–25 g/m² |
| | Triton ™ X-405 surfactant | 0.6–6 g/m² |
| | Estane ™ 5715 polyurethane | 0.5–5 g/m² |
| | Sodium α-ketoglutarate | 0.1–1 g/m² |
| | Sodium aspartate | 1.5–15 g/m² |
| | N—hexadecylpyridinium bromide | 0.3–3 g/m² |
| Subbing Layer | Poly(vinyl pyrrolidone) | 0.15–1.5 g/m² |
| Reagent Layer | Gelatin (hardened) | 3–30 g/m² |
| | Triton ™ X-405 surfactant | 0.15–1.5 g/m² |
| | Tris (hydroxymethyl)amino methane | 1.5–15 g/m² |
| | Lactate dehydrogenase | 300–3000 U/m² |
| | Malate dehydrogenase | 300–3000 U/m² |
| | NADH | 0.1–1 g/m² |
| | Pyridoxal-5-phosphate | 0.05–0.5 g/m² |
| /// /// | Poly(ethylene terephthalate) Support | //// //// |

These elements were evaluated for spreading/reagent layer cohesive strength by the procedure described hereinabove. The results, presented in Table II hereinbelow, show that the element of this invention exhibited substantial improvement in cohesive strength of the spreading/reagent layer over the Control element.

TABLE II

| Element | Cohesive Strength (mm to flake) | % Improvement |
|---|---|---|
| Control | 32 | — |
| Example 4 | 60 | 88% |

Both the Control element and the element of this invention were used to determine AST in serum samples. The incorporation of the quaternary ammonium compound in the spreading/reagent layer of the element of this invention did not adversely affect the determination of AST.

EXAMPLE 5

Element for Determination of Alanine Aminotransferase (ALT)

This is a comparative example like Example 4. An element for determining ALT was prepared having the format and components described for the AST element except that L-alanine was substituted for sodium aspartate in the spreading/reagent layer, and malate dehydrogenase was omitted from the reagent layer. A Control element was similarly prepared with the N-hexadecylpyridinium bromide omitted from the spreading/reagent layer. The results, presented in Table III hereinbelow, show that the element of this invention exhibited substantial improvement in cohesive strength of the spreading/reagent layer over the Control element.

TABLE III

| Element | Cohesive Strength (mm to flake) | % Improvement |
|---|---|---|
| Control | 57 | — |
| Example 5 | 100 | 75% |

Both the Control element and the element of this invention were used to determine ALT in serum samples. The incorporation of the quaternary ammonium compound in the spreading/reagent layer of the element of this invention did not adversely affect the determination of ALT.

EXAMPLE 6

Element for Determination of Serum Amylase

This is an example comparing an element of this invention useful for determination of amylase in a serum sample to a Control element prepared without a quaternary ammonium compound in the spreading/reagent layer. The element of this invention had the format and components shown hereinbelow. The Control element was similarly prepared but the EMCOL ™-CC36 compound was omitted from the spreading/reagent layer.

| | | |
|---|---|---|
| Spreading/ Reagent Layer | Titanium dioxide | 20–200 g/m² |
| | Cellulose acetate | 3–30 g/m² |
| | Brij ™-98 surfactant | 0.2–2 g/m² |
| | Triton ™ X-405 surfactant | 0.4–4 g/m² |
| | Estane ™ 5715 polyurethane | 0.5–5 g/m² |
| | KH₂PO₄ buffer | 0.6–6 g/m² |
| | NaH₂PO₄ buffer | 0.4–4 g/m² |
| | Dyed amylopectin* | 1–10 g/m² |
| | EMCOL ™-CC36 | 0.3–3 g/m² |
| Subbing Layer | Poly(vinyl pyrrolidone) | 0.15–1.5 g/m² |
| Reagent Layer | Gelatin (hardened) | 0.5–10 g/m² |
| | Poly(styrene-co-N—vinyl- | 0.1–2 g/m² |

| | -continued | |
|---|---|---|
| | benzyl-N—benzyl-N,N—dimethylammonium chloride-co-divinyl benzene) | |
| | $NaH_2PO_4$ (pH 6.8) buffer | 0.05–1 g/m² |
| | Triton ™ X-405 surfactant | 0.05–0.3 g/m² |
| //// | Poly(ethylene terephthalate) Support | //// //// |

*This is a dye starch complex prepared from amylopectin and Drimarine Red Z2B.

These elements were evaluated for cohesive strength of the blush polymer spreading/reagent layer according to the procedure described hereinabove. The results of the tests, shown in Table IV hereinbelow, indicate that the element of this invention had substantially improved cohesive strength over the Control element.

TABLE IV

| Element | Cohesive Strength (mm to flake) | % Improvement |
|---|---|---|
| Control | 9 | — |
| Example 6 | 27 | 300% |

The invention has been described in detail with particular reference to preferred embodiments thereof, but it will be understood that variations and modifications can be effected within the spirit and scope of the invention.

I claim:

1. A dry element for the analysis or transport of an aqueous liquid, said element comprising an isotropically porous zone which comprises a blush polymer having dispersed therein a particulate material, and a nonpolymeric heterocyclic, aliphatic or carbocyclic quaternary ammonium compound having at least 12 carbon atoms therein, which compound is present in said zone in an amount of at least about 2 weight percent, based on the dry weight of said blush polymer.

2. The element of claim 1 wherein the weight ratio of said particulate material to said blush polymer is from about 2:1 to about 20:1.

3. The element of claim 1 wherein said quaternary ammonium compound is represented by the structures (Ia and b):

$$\begin{array}{c} {}^{\prime\prime-R_2} \\ R_1-N^+-R_3 \quad X^- \\ | \\ R_4 \end{array} \quad \text{or} \quad \begin{array}{c} {}^{\prime-R_2}_{\phantom{N}+} \\ R_1=N=R_3 \quad X^- \\ | \\ R_4 \end{array}$$

Ia.    Ib.

wherein ===  represents a single or double bond; $R_1$, $R_2$, $R_3$ and $R_4$ are independently alkyl of 1 to 30 carbon atoms, $-(\text{alkylene-oxy})_n-H$ wherein said alkylene comprises 2 to 6 carbon atoms and n is an integer of 1 to 50; aryl of 6 to 14 carbon atoms, cycloalkyl of 5 to 20 carbon atoms, alkaryl of 7 to 30 carbon atoms, or a fluorocarbon group of 1 to 30 carbon atoms; provided that $R_1$, $R_2$, $R_3$ and $R_4$ together comprise at least 12 carbon atoms; or $R_1$ and $R_2$, taken together with the nitrogen atom, form a quaternary heterocyclic ring and $R_3$ and $R_4$ are as defined above and comprise together at least 12 carbon atoms; or $R_1$, $R_2$ and $R_3$, taken together with the nitrogen atom, form a quaternary heterocyclic ring and $R_4$ is as defined above and comprises at least 12 carbon atoms; and $X^-$ is a monovalent anion.

4. The element of claim 3 wherein $R_1$ is alkyl of 1 to 6 carbon atoms, $R_2$ is alkyl of 1 to 6 carbon atoms or $-(\text{alkylene-oxy})_n-H$ wherein said alkylene comprises 2 to 4 carbon atoms, and $X^-$ is halide or nitrate.

5. A dry analytical element for determination of an analyte in an aqueous liquid, said element comprising:
a support having thereon an isotropically porous zone which comprises a blush polymer having dispersed therein a particulate material, and a nonpolymeric heterocyclic, aliphatic or carbocyclic quaternary ammonium compound having at least 12 carbon atoms therein, which compound is present in said zone in an amount of at least about 2 weight percent, based on the dry weight of said blush polymer;
and said element containing an interactive composition for an analyte to be determined.

6. The element of claim 5 wherein said quaternary ammonium compound is represented by the structures (Ia and b):

$$\begin{array}{c} {}^{\prime\prime-R_2} \\ R_1-N^+-R_3 \quad X^- \\ | \\ R_4 \end{array} \quad \text{or} \quad \begin{array}{c} {}^{\prime-R_2}_{\phantom{N}+} \\ R_1=N=R_3 \quad X^- \\ | \\ R_4 \end{array}$$

Ia.    Ib.

wherein ===  represents a single or double bond; $R_1$, $R_2$, $R_3$ and $R_4$ are independently alkyl of 1 to 30 carbon atoms, $-(\text{alkylene-oxy})_n-H$ wherein said alkylene comprises 2 to 6 carbon atoms and n is an integer of 1 to 50; aryl of 6 to 14 carbon atoms, cycloalkyl of 5 to 20 carbon atoms, alkaryl of 7 to 30 carbon atoms, or a fluorocarbon group of 1 to 30 carbon atoms; provided that $R_1$, $R_2$, $R_3$ and $R_4$ together comprise at least 12 carbon atoms; or $R_1$ and $R_2$, taken together with the nitrogen atom, form a quaternary heterocyclic ring and $R_3$ and $R_4$ are as defined above and comprise together at least 12 carbon atoms; or $R_1$, $R_2$ and $R_3$, taken together with the nitrogen atom, form a quaternary heterocyclic ring and $R_4$ is as defined above and comprises at least 12 carbon atoms; and $X^-$ is a monovalent anion.

7. The element of claim 6 wherein $R_1$ is alkyl of 1 to 6 carbon atoms, $R_2$ is alkyl of 1 to 6 carbon atoms or $-(\text{alkylene-oxy})_n-H$ wherein said alkylene comprises 2 to 4 carbon atoms; and $X^-$ is halide or nitrate.

8. The element of claim 6 wherein said quaternary ammonium compound is a heterocyclic amine represented by the structure (Ib) wherein $R_1$, $R_2$ and $R_3$, taken together with the nitrogen atom, complete a 5 to 20-membered quaternary heterocyclic ring.

9. The element of claim 6 wherein said quaternary ammonium compound is selected from the group consisting of:

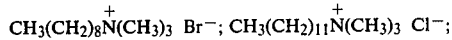

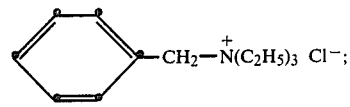

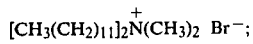

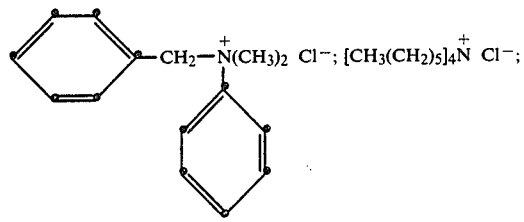

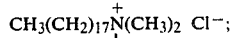

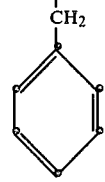

wherein n is 8, 25 or 41;

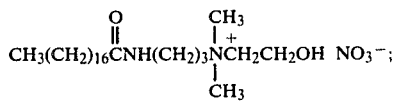

wherein R' is alkyl of 12, 14 or 16 carbon atoms; and

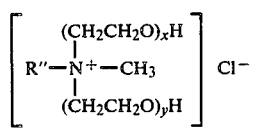

wherein R" is alkyl of 8 to 18 carbon atoms, x and y are independently integers of 2 to 50.

10. The element of claim 9 wherein said quaternary ammonium compound is

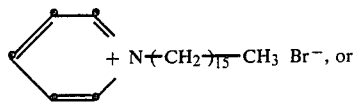

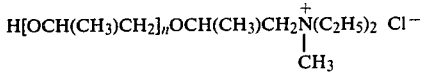

wherein n is 8 or 25.

11. The element of claim 5 wherein said quaternary ammonium compound is present in said porous zone in an amount of from about 8 to about 30 weight percent, based on the dry weight of said blush polymer.

12. A dry multizone analytical element for determination of an analyte in an aqueous liquid, said element comprising
a support having thereon, in order and in fluid contact,
a reagent zone containing at least one component of said composition, and
an isotropically porous spreading zone which comprises a blush polymer having dispersed therein a particulate material, and a nonpolymeric heterocyclic, aliphatic or carbocyclic quaternary ammonium compound which is present in said zone in an amount of at least about 2 weight percent, based on the dry weight of said blush polymer;
wherein said quaternary ammonium compound is represented by the structures (Ia and b):

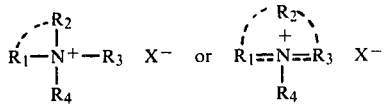

Ia.                     Ib.

wherein ===== represents a single or double bond; $R_1$, $R_2$, $R_3$ and $R_4$ independently alkyl of 1 to 30 carbon atoms,

wherein said alkylene comprises 2 to 6 carbon atoms and n is an integer of 1 to 50; aryl of 6 to 14 carbon atoms, cycloalkyl of 5 to 20 carbon atoms, alkaryl of 7 to 30 carbon atoms, or a fluorocarbon group of 1 to 30 carbon atoms; provided that $R_1$, $R_2$, $R_3$ and $R_4$ together comprise at least 12 carbon atoms; or $R_1$ and $R_2$, taken together with the nitrogen atom, form a quaternary heterocyclic ring and $R_3$ and $R_4$ are as defined above and comprise together at least 12 carbon atoms; or $R_1$, $R_2$ and $R_3$, taken together with the nitrogen atom, form a quaternary heterocyclic ring and $R_4$ is as defined above and comprises at least 12 carbon atoms; and $X^-$ is a monovalent anion;
and said element containing an interactive composition for an analyte to be determined.

13. The element of claim 12 wherein said particulate material is titanium dioxide or barium sulfate.

14. The element of claim 13 wherein said spreading layer comprises cellulose acetate.

15. The element of claim 12 wherein said analyte is aspartate aminotransferase and said interactive composition comprises NADH, L-aspartate, α-ketoglutarate, lactate dehydrogenase, malate dehydrogenase and pyridoxal phosphate, or said analyte is alanine aminotransferase and said interactive composition comprises NADH, L-alanine, α-ketoglutarate, lactate dehydrogenase and pyridoxal phosphate.

16. A method for the determination of an analyte in an aqueous liquid, said method comprising the steps of:
   A. physically contacting a sample of said liquid together with an interactive composition for said analyte and a dry analytical element to provide a detectable change,
   said element comprising an isotropically porous zone which comprises a blush polymer having dispersed therein a particulate material, and a nonpolymeric heterocyclic, aliphatic or carbocyclic quaternary ammonium compound having at least 12 carbon atoms therein, which compound is present in said zone in an amount of at least about 2 weight percent, based on the dry weight of said blush polymer; and
   B. measuring said detectable change.

17. The method of claim 16 wherein said quaternary ammonium compound is represented by the structures (Ia and b):

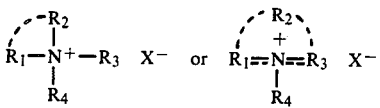

wherein  represents a single or double bond; $R_1$, $R_2$, $R_3$ and $R_4$ are independently alkyl of 1 to 30 carbon atoms, $-(\text{alkylene-oxy})_n-H$ wherein said alkylene comprises 2 to 6 carbon atoms and n is an integer of 1 to 50; aryl of 6 to 14 carbon atoms, cycloalkyl of 5 to 20 carbon atoms, alkaryl of 7 to 30 carbon atoms, or a fluorocarbon group of 1 to 30 carbon atoms; provided that $R_1$, $R_2$, $R_3$ and $R_4$ together comprise at least 12 carbon atoms; or $R_1$ and $R_2$, taken together with the nitrogen atom, form a quaternary heterocyclic ring and $R_3$ and $R_4$ are as defined above and comprise together at least 12 carbon atoms; or $R_1$, $R_2$ and $R_3$, taken together with the nitrogen atom, form a quaternary heterocyclic ring and $R_4$ is as defined above and comprises at least 12 carbon atoms; and $X^-$ is a monovalent anion.

18. The method of claim 17 wherein said detectable change is in the rate of formation of a detectable species.

19. The method of claim 17 wherein said detectable change is in the rate of disappearance of a detectable species.

20. The method of claim 17 wherein said interactive composition is in said element.

* * * * *